United States Patent [19]

Uhlen

[11] Patent Number: 5,712,125
[45] Date of Patent: Jan. 27, 1998

[54] COMPETITIVE PCR FOR QUANTITATION OF DNA

[75] Inventor: Mathias Uhlen, Uppsala, Sweden

[73] Assignee: CEMV Bioteknik AB, Uppsala, Sweden

[21] Appl. No.: 459,519

[22] Filed: Jun. 2, 1995

Related U.S. Application Data

[63] Continuation of Ser. No. 987,285, filed as PCT/EP91/01398, Jul. 23, 1991, abandoned.

[30] Foreign Application Priority Data

Jul. 24, 1990 [GB] United Kingdom ............... 9016163

[51] Int. Cl.[6] .......................................... C12P 19/34
[52] U.S. Cl. ................................ 435/91.2; 435/810
[58] Field of Search ......................... 435/91.2, 6, 810

[56] References Cited

U.S. PATENT DOCUMENTS

| 4,654,267 | 3/1987 | Ugelstad et al. | 428/407 |
|---|---|---|---|
| 4,777,129 | 10/1988 | Dattagupta et al. | 435/6 |
| 5,213,961 | 5/1993 | Bunn et al. | 435/6 |
| 5,219,727 | 6/1993 | Wang et al. | 435/6 |

FOREIGN PATENT DOCUMENTS

| 0198662 | 10/1986 | European Pat. Off. | 435/6 |
|---|---|---|---|
| 89/09282 | 10/1989 | WIPO | |
| 90/06043 | 6/1990 | WIPO | |
| 90/11369 | 10/1990 | WIPO | |
| 91/02817 | 3/1991 | WIPO | |
| WO9323562 | 11/1993 | WIPO | C12Q 1/68 |
| WO9409156 | 4/1994 | WIPO | C12Q 1/68 |

OTHER PUBLICATIONS

Mullis et al. Cold Spring Harb:Symp. Quant. Biol 51:263–273(1986).
Venetianer et al. PNAS, USA 71(10):3892–3895(Oct. 1974).
Higuchi et al. Nucl. Acids Res. 16(15):7351–7367(1988).
Yun et al. (1994) J. Virol. Methods 47:1–14.
Belak et al. (1993) Mol. Cell. Probes 7:241–48.
Friedhoff et al. (1993) Anal. Biochem. 215:9–16.
Rhoer-Moja et al. (1994) Nucl. Acids Res. 22:547–48.
Kapperud et al. (1993) Appl. Envir. Microbiol. 59:2938–44.
Olsvik et al. (1991) Mol. Cell. Probes 5:429–35.
Wahlberg et al. (1990) Proc. Natl. Acad. Sci. USA 87:6569–73.
G. Gilliland, et al, "Analysis of Cytokine mRNA and DNA: Detection and Quantitation by Competitive Polymerase Chain Reaction", Proc. Natl. Acad. Sci., vol. 87, 1990, pp. 2725–2729.
G. Gilliland, et al, "Competitive PCR for Quantitation of MRNA", PCR Protocols: A Guide to Methods and Applications, 1990, pp. 60–69.

(List continued on next page.)

*Primary Examiner*—W. Gary Jones
*Assistant Examiner*—Amy Atzel
*Attorney, Agent, or Firm*—Foley & Lardner

[57] ABSTRACT

The invention provides a method of determining the amount of target DNA in a sample which comprises the steps of (a) dividing the sample into a plurality of aliquots; (b) adding to each aliquot a known amount of competitor DNA which is the same as the target DNA except that it comprises a recognition site capable of being detected directly or indirectly by a labelled species whereby the ratio of target DNA to competitor DNA is different in the aliquots; (c) co-amplifying the target DNA and competitor DNA in each aliquot by the polymerase chain reaction (PCR) using at least one primer which permits immobilization of the co-amplified DNA, the annealing sites of any PCR primers used being outward of the recognition site; (d) labelling the amplified competitor DNA; (e) before or after step (d), immobilizing the co-amplified DNA where not already immobilized, via at least one PCR primer; (f) assessing the amount of label on the immobilized amplified competitor DNA in each aliquot to provide an indication of the amount of target DNA in the sample.

16 Claims, 4 Drawing Sheets

OTHER PUBLICATIONS

M. Becker-Andre, et al., "Absolute mRNA Quantification Using the Polymerase Chain Reaction (PCR)". *Nucleic Acids Research*, vol. 17, No. 22, 1989.

Syvänen, A. et al., "Quantification of Polymerase Chain Reaction Products by Affinity-Based Hybrid Collection", *Nucleic Acids Research*, vol. 16, pp. 11327–11337 (1988).

Lundeberg, J. et al., "Laboratory Methods: Rapid Colorimetric Detection of In Vitro Amplified DNA Sequences", *DNA and Cell Biology*, vol. 9, pp. 287–292 (1990).

Zolg, J. W. et al., "High Salt Lysates: A Simple Method to Store Blood Samples Without Refrigeration for Subsequent Use with DNA Probes", *Am. J. Trop. Med. Hyg.*, 39(1), pp. 33–40 (1988).

Hultman, T. et al., "Direct Solid Phase Sequencing of Genomic and Plasmid DNA Using Magnetic Beads as Solid Support", *Nucleic Acids Research*, vol. 17, pp. 4937–4946 (1989).

Holmberg, M. et al., "A Comparison of Two DNA Probes, One Specific for *Plasmodium falciparum* and One with Wider Reactivity, in the Diagnosis of Malaria", Trans. R. Soc. Trop. Med. Hyg., 84, 202 (1990).

Favaloro, J. M. et al., "Structure of the RESA Gene of *Plasmodium falciparum*", *Nucl. Acids Res.* 14, pp. 8265–8277 (1986).

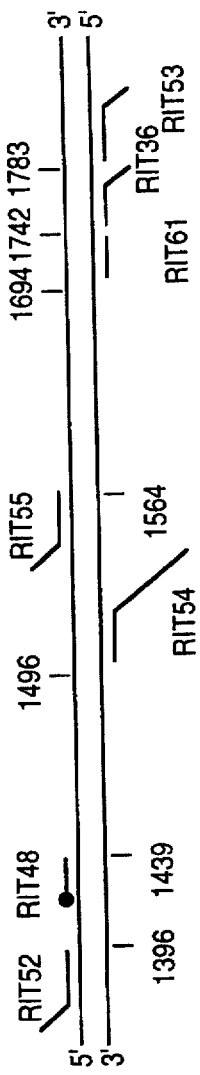

| PRIMER | SEQUENCE | INTRODUCING |
|---|---|---|
| RIT52 | 5'-CGGAATTCCCTCCCTCCTGATATTGATCATAC-3' | EcoRI |
| RIT48 | 5'-BIOTIN-GTTCATGACTGATGTAAATA-3' | biotin |
| RIT54 | 5'-GGGGATCCTAATTGTTATCCGCTCACAATTAAAAGAACTTTATCTACAATAAG-3' | BamHI+lac operator site |
| RIT55 | 5'-GGGGATCCGGAAGAAGTGAGGAGACATT-3' | BamHI |
| RIT61 | 5'-GTGTCCATTTGCTCTCATATGC-3' | |
| RIT53 | 5'-AGAAGCTTAATATTTCTGCCTGTACCAG-3' | HindIII |
| RIT36 | (SEE PCT/EP90/00454, PAGE 4, LINE 31) | lac operator site |

COMPETITIVE PCR FOR QUANTITATION OF DNA

This application is a continuation of application Ser. No. 07/987,285, filed as PCT/EP91/01398 Jul. 23, 1991 now abandoned.

This invention relates to a method of quantifying DNA in particular a method of solid phase diagnosis of medical conditions by the identification of specific DNA.

Target DNA molecules are often present in cell lysates or other source materials in extremely small quantities and in order to amplify such DNA selectively, the polymerase chain reaction (PCR) method has been developed. In this technique a pair of polymerisation primers specific to known sequences of the target DNA are selected, one hybridising at or near the 5' end of the coding strand and the other at or near the 5' end of the non-coding strand such that in the presence of a polymerase, each primer produces a DNA sequence extending the full length of the target DNA template. If the DNA so produced is then subjected to strand separation, typically by melting at a temperature of about 90° C., the newly formed single stranded DNA sequences will hybridise to excess primer present in the mixture, usually after reducing the temperature to the range suitable for annealing, whereupon in the presence of the polymerase, further DNA strands are synthesised, this time extending only between the termini of the two primers. The polymerase is preferably capable of surviving the high temperature used in the strand separation step, a suitable thermophilic polymerase, namely Taq, having recently become available. If an excess of the two primers and of nucleotides needed for DNA synthesis is maintained in the medium, it is possible to operate a repeated cyclic process in which the separate strands are synthesised, separated, annealed to primer and new strands synthesised, merely by raising and lowering the temperature between the optimal temperatures for each of the above stages. In this way, it is found that amplification of the original target DNA can be exponential and million-fold increases of concentration can be effected in a relatively short time.

However, this procedure is not always sufficiently selective due to a percentage of non-specific binding of the primers to other DNA sequences, thereby amplifying the latter in addition to the target DNA. Moreover, there is a need to establish how much target DNA was present in a sample before PCR amplification.

In the detection of bacteria, virus and parasites for example PCR has several advantages compared to conventional diagnostic methods, i.e. the generality and speed of the assay. However, the fact that conventional PCR assays are only qualitative limits their use to diagnostic applications where only the presence or absence of the pathogen is to be determined. For many diseases, a quantitative measurement is need to make a proper diagnosis and advantageously it would be useful to be able to measure the amount of pathogen during treatment to make a relevant prognosis. As mentioned above, there is major concern regarding the usefulness of PCR assay because their extreme sensitivity makes it possible to obtain false positives as a result of single molecules contaminating the sample. There is a need for a quantitative assay, e.g. one suitable for clinical assays, which overcomes the drawbacks associated with conventional PCR assays.

Recently, several systems to quantify the initial template DNA/RNA have been described (A. C. Syvänen, M. Bengtström, J. Tenhunen and H. Söderlund Nucl. Acids Res., 16, 11327 (1988); G. Gilliland, S. Perrin and H. F. Bunn PCR protocols, pp. 60–69, Academic Press, San Diego (1990); and M. Becker-André and K. Hahlbrock, Nucl. Acids Res. 17,9437 (1990)). Affinity-based hybrid collection of isotope-labelled products has been used to determine the amount of DNA synthesized after various PCR cycles (A. C. Syvänen et al. supra). This method allows for indirect determination of the initial number of target templates in the sample. However, since the efficiency of PCR varies with changes in inter alia template and nucleoside concentration, quality of polymerase etc it is difficult to establish standard conditions which would lend themselves to use in automatic or semi-automatic equipment.

Co-amplification of cDNA and chromosomal DNA has also been performed, where the genomic DNA includes a small intron sequence (G. Gilliland et al. supra). Thus, a size difference is obtained, which can be used for electrophoretic separation to determine the ratio of genomic DNA versus cDNA. Whilst the technique overcomes some of the problems associated with Syvänen et al., the method can only be used for special applications and quantification of different sized fragments is needed.

Another quantitative method is PCR aided transcript titration assay (PATTY) in which the amount of RNA is measured by adding mutated RNA to the sample, which contains or lacks a restriction site in the amplified region as compared to the target RNA (M. Becker-André supra). After cDNA synthesis, by reverse transcriptase followed by PCR the co-amplified product is thereafter restricted and analyzed by electrophoresis. The relative amount of cleaved material gives the ratio of target RNA to internal standard RNA. This method has the disadvantages that electrophoresis or restriction analysis are needed.

Earlier we described a solid phase approach for detection of immobilized amplified nucleic acids, designated DIANA (PCT/EP90/00454), which has been used for example in its preferred embodiment in the colorimetric detection of in vitro amplified DNA. The assay is based on the use of a biotinylated or otherwise functionalised PCR primer, which is used to capture in vitro amplified material on, for example, streptavidin-coated magnetic beads. The other PCR primer contains a "handle", such as a lac operator sequence, allowing colorimetric detection of the captured DNA using a LacI repressor-β-galactosidase fusion protein. J. Lundeberg, J Wahlberg, M Holmberg, U Pettersson and M. Uhlen. DNA Cell Biol. 9 (4) 289 (1990)). W. Zolg, E. Scott and M. Wendlinger Am. J. Trop. Med. Hyg. 39(1), 33 (1988). The preferred form of the qualitative DIANA assay combines the advantages of the PCR method with the high specificity and stability of the biotin-streptavidin system and the simplicity of a colorimetric detection based on β-galactosidase. The strong interaction between biotin and streptavidin ($K_d=10^{-15}$ $M^{-1}$) accentuates the efficiency of the system. The magnetic beads as solid support ensure that no centrifugations, filtrations or precipitations are needed. (T. Hultman, S. Ståhl, E. Hornes and M. Uhlén Nucl. Acids Res. 17, 4937 (1989).

We have now discovered a method for quantifying DNA, particularly a method for determining the amount of target DNA which was present in a sample before PCR. Our method is based on competitive titration wherein amounts of target DNA are co-amplified with known amounts of competitor DNA to produce different ratios of target: competitor DNA, the competitor DNA being substantially the same as the target DNA except that is comprises a recognition site which may be detected directly or indirectly by a labelled species. Unlike the method of Becker-Andre we do not involve restriction cleavage and electrophoretic analysis.

According to the present invention there is provided a method of determining the amount of target DNA in a sample which comprises the steps of (a) dividing the sample into a plurality of aliquots;

(b) adding to each aliquot a known amount of competitor DNA which is the same as the target DNA except that it comprises a recognition site capable of specifically binding to a detector molecule which may be linked directly or indirectly to a label whereby the ratio of target DNA to competitor DNA is different in the aliquots;

(c) co-amplifying the target DNA and competitor DNA in each aliquot by the polymerase chain reaction (PCR) using at least one primer which permits immobilisation of the co-amplified DNA, the annealing sites of any PCR primers used being outward of the recognition site, (d) binding said detector molecule to the amplified competitor DNA whereby said DNA is labelled;

(e) before or after step (d), immobilising the co-amplified DNA where not already immobilised, via at least one PCR primer;

(f) assessing the amount of label on the immobilised amplified competitor DNA in each aliquot to provide an indication of the amount of target DNA in the sample.

References herein to "target DNA" are intended to encompass inter alia cDNA e.g. from retroviral RNA, genomic DNA, mitochondrial DNA etc.

Performance of the method according to the invention produces a set of label values which, when plotted against the known amounts of added competitor DNA give a characteristic sigmoid curve (as will be more fully appreciated from the examples which follow); the point of inflection on the curve is defined by the sharp change in the amount of labelled DNA between those aliquots in which added competitor DNA predominated and those in which target DNA predominated and is approximately proportional to the amount of target DNA in the initial sample.

In general it is preferable to add different known amounts of the competitor DNA to identical aliquots of the sample, so that any possible effect of inhibitors is unchanged. The competitor DNA is most conveniently added to the aliquots as a series of equally stepped dilutions, eg 1:3 or, for a more accurate result, 1:1.5. However, much higher dilutions may be useful, for example, as high as 1:100, for some purposes. About 6–10 such dilutions normally give an adequate range and 8×12 microliter wells may be used for this purpose. It is usually sufficient for diagnostic purposes to conclude that the amount of target DNA lies between the amounts of competitor DNA in two or possibly three adjacent dilutions. The method of the invention thus avoids the need for determination of the actual amount of amplified target DNA although this may in some cases be useful information.

Two-stage PCR (using nested primers), as described in our co-pending application PCT/EP90/00454, may be used to enhance the signal to noise ratio and thereby increase the sensitivity of the method according to the invention.

Regardless of whether one-stage or two stage PCR is performed, the efficiency of the PCR is not critical since the invention relies on the sharp change in the amount of labelled DNA between different aliquots. However, it is preferred to run a qualitative DIANA as a check for the presence or absence of target DNA and if run under identical conditions enables the total quantity of amplified DNA to be determined and related to the quantitative DIANA assay.

Under certain circumstances, it may be sufficient from a diagnostic point of view, to determine merely whether the amount of target DNA is above or below a critical level, for example that derived from 1000 target pathogens. In this case, PCR may be effected on a single sample to which a known amount of the competitor DNA is added at the known critical level. Where the amount of target DNA is significantly greater than the amount of competitor DNA, the signal from the amplified and labelled competitor DNA will be characteristically low.

Immobilisation of the co-amplified DNA may either take place as part of the PCR amplification itself, as where one or more primers are attached to a support, or alternatively one or more of the primers may carry a functional group permitting subsequent immobilisation, eg. a biotin or thiol group. Where a subsequent immobilisation step is used, this may be effected before labelling, thus permitting washing of the immobilised amplified DNA prior to labelling, or after the labelling step. In either case, unattached label will be removed from the immobilisation labelled DNA prior to assessment.

The solid support may conveniently take the form of microtitre wells, which are advantageously in the conventional 8×12 format, or dipsticks which may be made of polystyrene activated to bind the primer DNA (K Almar, Doctoral Theses, Royal Institute of Technology, Stockholm, Sweden, 1988). The support may also comprise particles, fibres or capillaries made, for example, of agarose, cellulose, alginate, a highly stable thermoplastic tetrafluorethylene homopolymer such as "TEFLON" or polystyrene. The support may also comprise magnetic particles eg the superparamagnetic beads produced by Dynal AS (Oslo, Norway).

Preferably sufficient cycles of PCR are performed so that a saturation level is achieved; in that way the amplified DNA contains substantially the same ratio of target DNA to competitor DNA as that present before PCR.

It is advantageous to provide conditions such that the competitor and target DNA are amplified equally efficiently by PCR and it is therefore important that the size and GC-content of each fragment is kept substantially the same and that the sequences where the primers anneal are identical. In some instances it will also be necessary to take into account the efficiency of the cell lysis of the sample which can make some of the genomic DNA less available for the PCR. In addition, the target DNA may be part of chromosomal DNA in the initial cycles, while the competitor DNA may be, for example, in the form of a small plasmid. Thus it might be necessary to adjust for the relative amplification efficiencies of these early PCR cycles.

The quantitative method according to the invention may be used for general quantification of RNA and DNA both for research and clinical applications, including diagnosis of viral, bacterial and protozoan pathogens. It may also find applications in forensic medicine. The assay technique is very simple and rapid, thus making it easy to automate by using a robot apparatus where a large number of samples may be rapidly analysed. Since the preferred detection and quantification is based on a colorimetric reaction a visual analysis is often sufficient for evaluation.

Any suitable polymerase may be used, although it is preferred to use a thermophilic enzyme such as Taq polymerase to permit the repeated temperature cycling without having to add further polymerase, e.g. Klenow fragment, in each cycle.

As mentioned above, the target DNA may be cDNA synthesised from mRNA in the sample and the method of the invention is thus applicable to diagnosis on the basis of characteristic mRNA. Such preliminary synthesis can be carried out by a preliminary treatment with a reverse transcriptase, conveniently in the same system of buffers and bases to be used in the subsequent PCR steps. Since the PCR procedure requires heating to effect strand separation, the reverse transcriptase will be inactivated in the first PCR cycle. When mRNA is the target nucleic acid, it may be advantageous to submit the initial sample, e.g. a serum sample, to treatment with an immobilised polydT oligonucleotide in order to retrieve all mRNA via the terminal polyA sequences thereof. Alternatively, a specific oligonucleotide sequence may be used to retrieve the RNA via a specific RNA sequence. The oligonucleotide can then serve as a primer for cDNA synthesis, as described in International Patent Application PCT/89EP/00304.

The recognition site may be introduced into the competitor DNA by in vitro mutagenesis of a sample of the target DNA, e.g. by the method described in International Application PCT/EP89/01417.

The recognition site on the competitor DNA is preferably small and exhibits a high binding specificity with the detector molecule which directly or indirectly attaches the label. For example, the recognition site could be a unique sequence recognised by a DNA probe. Such a probe could be radio-labelled, for example, or be 5' end labelled using fluorescence. It is preferred however, to insert a site into the competitor DNA which is recognised by a protein.

A number of proteins are known which bind to specific DNA sequences and are often involved in genetic processes such as switching operons on and off. One such protein is the lac repressor LacI which reacts with the lac operon (lacOP) to inhibit transcription. Thus, if the recognition site is the DNA sequence lacOP, the label can be attached via the protein LacI. It is particularly convenient to devise a fusion protein of a DNA binding protein such as LacI with a further protein which can be subsequently used for detection for example using methods based on colour fluorescence or chemiluminescence. Examples of such proteins are β-galactosidase, alkaline phosphatase and peroxidase.

It is preferred to use as a label a LacI repressor-β-galactosidase fusion protein which recognises a 21 base pair lac operator sequence introduced into the competitor DNA, e.g. near the middle. The fusion protein will bind to the competitive DNA and the addition of o-Nitrophenyl-β-D-Galactopyranoside ("ONPG") will lead to a colour formation which can be assessed spectrophotometrically. Use of this fusion protein and IPTG allows for a fast simple colorimetric assay which does not have the safety problems associated with using radio-labels.

The specificity of the process for the target DNA is greatly increased by including a first-stage PCR amplification step. By such preliminary amplification, the concentration of target DNA is greatly increased with respect to other DNA which may be present in the sample and a second-stage amplification with at least one primer specific to a different sequence of the target DNA, as described in PCT/EP 90/00454, significantly enhances the signal due to the target DNA relative to the 'background noise'.

The method of the present invention is particularly advantageous in diagnosis of pathological conditions characterised by the presence of specific DNA, particularly latent infectious diseases such as viral infection by herpes, hepatitis or HIV. Also, the method can be used with advantage to characterise or serotype and quantify bacterial, protozoal and fungal infections where samples of the infecting organism maybe difficult to obtain or where an isolated organism is difficult to grow in vitro for subsequent characterisation as in the case of *P. falciparum* or *chlamydia species*. Due to the method's simplicity and speed it may also be used to detect other pathological agents which cause diseases such as gonorrhoea and syphilis. Even in cases where samples of the infecting organism may be easily obtained, the speed of the PCR technique compared with overnight incubation of a culture may make the method according to the invention preferable over conventional microbiological techniques.

The solid support may carry functional groups such as hydroxyl, carboxyl, aldehyde or amino groups, or other moieties such as avidin or streptavidin, for the attachment of primers. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

The invention also comprises kits for carrying out the method of the invention. These will normally include at least the following components:

(a) competitor DNA comprising a recognition site which is capable of specifically binding to a detector molecule which may be linked directly or indirectly to a label;

(b) a detector molecule for binding to amplified competitor DNA whereby said DNA is labelled;

(c) a pair of primers for PCR at least one primer having means permitting immobilisation of said primer;

(d) a polymerase which is preferably heat stable, for example Taq1 polymerase;

(e) buffers for the PCR reaction; and (f) optionally a solid support.

Where an enzyme label is used, the kit will advantageously contain a substrate for the enzyme and other components of a detection system.

The invention will now be described by way of non-limiting examples with reference to the drawings in which:

FIG. 2 is a diagram showing various primer sequences (SEQ ID NOS 1–6), their designations and their relationship to a target sequence.

Figure 1:
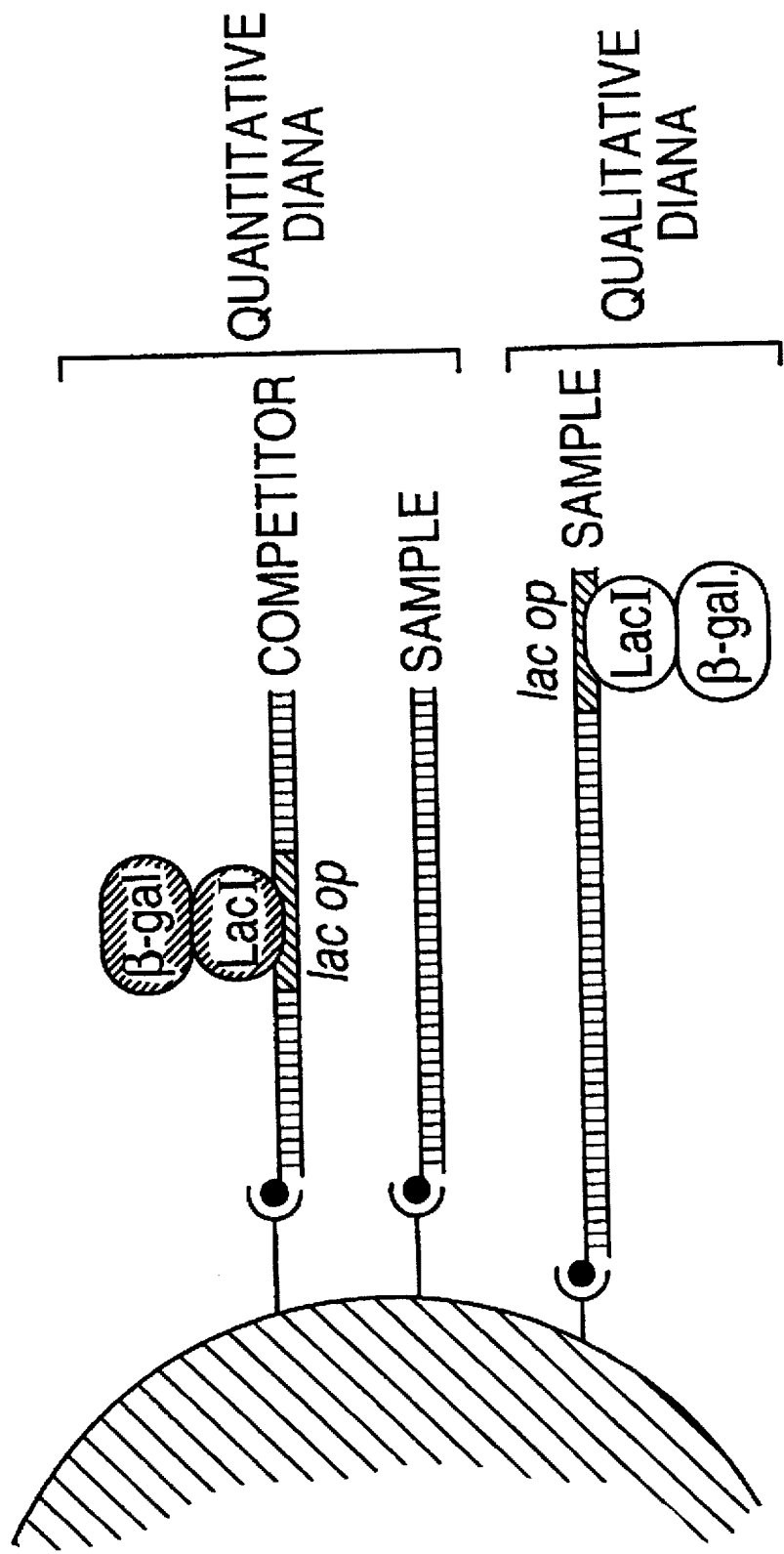
FIG. 1 shows schematically a difference between a preferred method of qualitative DIANA and a preferred method of quantitative DIANA according to the invention.

FIG. 1 schematically shows a preferred embodiment of the principle of the quantitative DIANA according to the invention, in which a solid support is used to immobilise biotinylated DNA fragment obtained after PCR and a LaCI repressor-β-galactosidase fusion protein is used for the subsequent colorimetric detection. In the qualitative DIANA assay a lac operator sequence is incorporated into the in vitro amplified material using a "handle" sequence in one of the PCR primers. In the quantitative DIANA assay, a lac operator sequence is instead introduced into a cloned version of the target sequence that is competitive DNA and a known amount of this cloned DNA is co-amplified with the target DNA. In both cases, the detection is based on the specific interaction of the LacI-β-galactosidase fusion protein (J. Wahlberg et al. supra), with the lac operator sequence and the subsequent hydrolysis of the substrate orthonitrophenyl-β-D-galactoside (ONPG), to give the colorimetric response.

EXAMPLE I

Determination of the Absolute Amounts of the Parasite *Plasmodium falciparum* in Clinical Human Blood Samples The Pf155 gene was chosen as target DNA since amplification of this gene had been shown to accurately detect the presence of parasite in clinical material (J. Lundeberg, J. Wahlberg, M. Holmberg, U. Pettersson and M. Uhlén DNA Cell Biol. 9(4), 289 (1990)). The primers used to clone and assay the Pf155 gene are shown in FIG. 2. Primers RIT52, 53, 54 and RIT55 were used to clone the whole fragment by PCR. Template for the cloning competitive DNA was a clinical sample from The Gambia (M. Holmberg et al. Trans. R. Soc. Trop. Med. Hyg. 84, 202 (1990) and a 21 base pair lac operator sequence was simultaneously introduced into the cloned fragment, replacing 21 nucleotides from 1519 to 1539 of the gene.

FIG. 2 shows the structure of the Pf155/RESA target gene of P. falciparum and the primers (SEQ ID NOS 1–6) used for the detection, quantification and cloning. The numbers refer to the published sequence by J. M. Favaloro et al., Nucl. Acids Res 14, 8265 (1986). The primers were synthesized by phosphoramidite chemistry on an automated DNA synthesis machine (GENE ASSEMBLER PLUS, Pharmacia, Sweden). The PCR cloning and in vitro mutagenesis was performed by subcloning the upstream fragment of Pf155/RESA gene generated by PCR with primers RIT52 and RIT54 and cleaved with BamHI and EcoRI and ligated into pUC8 digested with the same enzymes. The resulting construction was digested with BamHI and HindII to enable ligation with the downstream fragment generated by PCR and RIT53 and RIT55, digested with BamHI and HindIII. The mutant clone was verified by DNA sequencing as described by T Hultman et al., Nuc Acids Res 17, 4937 1989. For the qualitative assay, RIT48 and RIT36 were used, while primers RIT48 and RIT61 were used for the quantitative DIANA. The nucleotides shown in italics correspond to sequences introduced by in vitro mutagenesis.

For the quantitative DIANA, a two step nested primer PCR was performed using the outer primers RIT52 and RIT53 for an initial 35 cycles and then, after dilution of the amplified material, an additional 25 cycles with the inner primers RIT48 and RIT61. The cloned competitor DNA was added in serial dilutions before the first PCR cycle to tubes containing the same amount of the initial target DNA. A standard qualitative DIANA was run in parallel without the addition of competitor DNA. In this case, the downstream primer RIT61 was replaced with primer RIT36 containing a lac operator "handle" sequence. The hybridization site of RIT36 is shown in FIG. 2. The sequence of RIT36 is set forth in PCT/EP90/00454 on page 4, at line 31, for instance. Thus, a qualitative assay to detect the presence or absence of the Pf155 gene is performed in parallel with the quantitative assay.

A lysis mixture W. Zolg, E. Scott and M. Wendlinger Am. J. Trop. Med. Hyg 39 (1) 33 (1988) corresponding to 0.2 µl whole blood of patients from The Gambia were used and the amount of parasites were independently determined by microscopical determination.

The in vitro amplification was performed using a Techne Programmable DRI-BLOCK PHC-2 (Techne, U. K.). The amplification was run in two consecutive steps; first 35 cycles with RIT52 and RIT53, followed by a 1/100 dilution and a second amplification for 25 cycles with RIT48 and RIT61 for the quantitative DIANA assay and RIT48 and RIT36 for the qualitative DIANA assay. The PCR buffer used contained 20 mM TAPS (3-[tris(hydroxymethyl)methylamino]-1-propanesulfonic acid)(pH 9.3), 8 mM $MgCl_2$, 50 mM KCl and 0.1% Tween 20. The Sample and a decreasing amount of competitor DNA, 1 µl each, were put into PCR tubes with 10 µl PCR buffer. The tubes were subsequently heated to 99° C. for 5 minutes to lyse the cells and then rapidly cooled to 0° C. To the lysed mixture, 40 µl of a PCR buffer with 0.2 mM dNTP, 0.2 µM of each primer and 1.0 unit of AMPLITAQ polymerase (Perkin Elmer, Sweden) was added. The reaction mixture was covered with a layer of light mineral oil (Sigma, USA). One temperature cycle on the PCR was: denaturation of template 96° C., 0.5 minute; annealing of primers 59° C., 1 minute; extension of primers 72° C., 1 minute. The PCR mixture was immobilized to 300 µg of magnetic beads with covalently coupled streptavidin, DYNABEADS M280-STREPTAVIDIN (Dynal A S, Norway) and incubated for 20 minutes at room temperature. The beads, with the immobilized DNA, were mixed with 200 µl of fusion protein (Lac I-β-galactosidase, 0.2 mg/ml and 200 µg of sonicated herring sperm DNA in a Eppendorf tube for 20 minutes. The beads were washed four times with 250 µl TST buffer (0.1M Tris-HCl, pH 7.5, 0.15M NaCl, 0.1% Tween 20) containing 10 mM β-mercaptoethanol. The substrate, ortho-nitrophenyl-β-D-galactoside (ONPG), was added (200 µl ) and the change of absorbance at room temperature was measured. The reaction was stopped by taking half of the reaction mixture to a microtitre plate with stop solution. The result is presented as the change of absorbance per minute at 405 nm.

In FIG. 3, A is a titration curve with 1:1.5 serial dilution of competitor DNA using a sample containing 500 parasites and B,C,D,E each show quantitative DIANA of samples using a 1:3 serial dilution of the competitor DNA with the amount of parasites per sample determined by the microscopical method indicated. Lane "+/−" represents the qualitative DIANA detection of the respective sample. A titration curves is used to obtain a range of values for the amount of target DNA present in the sample. The endpoints of this range are determined from the inflection point of the titration curve. The inflection point occurs where the amount of amplified target DNA is equal to the amount of amplified competitor DNA, and is observed as a sharp decrease in the amount of labeled competitor DNA detected.

Figure 3A:
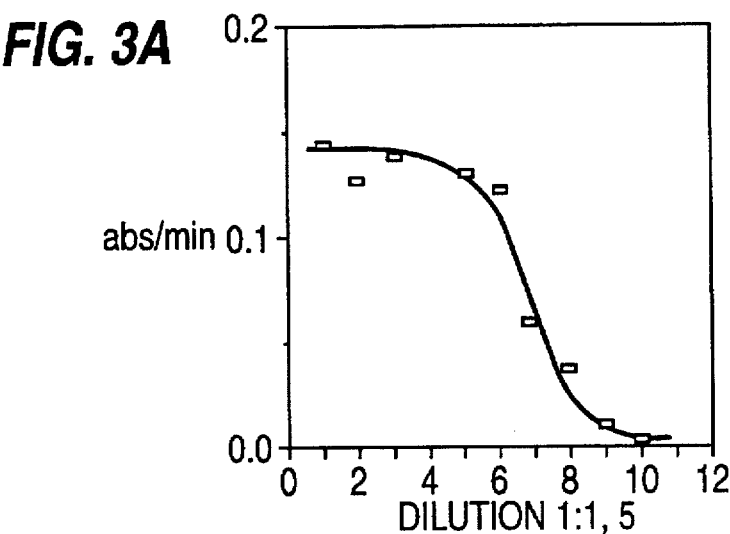
FIG. 3 shows graphically the results of experiments described below.

Initially a sample containing approximately 500 parasites (target DNA molecules) used as a template to generate a standard curve for the quantitative DIANA (FIG. 3A) and 1:1.5 serial dilutions of the competitor DNA containing lac operator sequence were performed, starting with approximately 16000 competitor plasmid molecules in the first step (dilution 1). Note that since the parasite is haploid in its asexual stage, there is only 1 target chromosomal region per parasite. After a two step PCR procedure, biotin-containing material was immobilised by the magnetic beads. The beads were washed and fusion protein and chromogenic substrate was added. The results, presented in FIG. 3A, shows that dilutions 1 to 6 gives a high colorimetric response showing that most DNA fragments originate from the lac operator-containing competitor. In contrast, a low activity is observed for dilutions 9 to 10 showing that the target DNA, lacking the lac operator, is in majority. A intermediate response is obtained for dilution 7 and 8. Thus, the inflection point of this curve occurs between dilutions 7 and 8 which contain approximately 1400 and 950 competitor molecules, respectively. This shows that the quantitative DIANA assay gives a titration curve with the expected sigmoid shape. Because the sample is known to contain approximately 500 parasites (target DNA molecules), these results indicate that the plasmid competitor DNA is amplified with an approximately two-fold lower efficiency as compared to the genomic target DNA. This 2:1 relationship is used below to determine the amount of target DNA present in the samples whose titration curves are set forth in FIGS. 3B–3E.

Figure 3B:
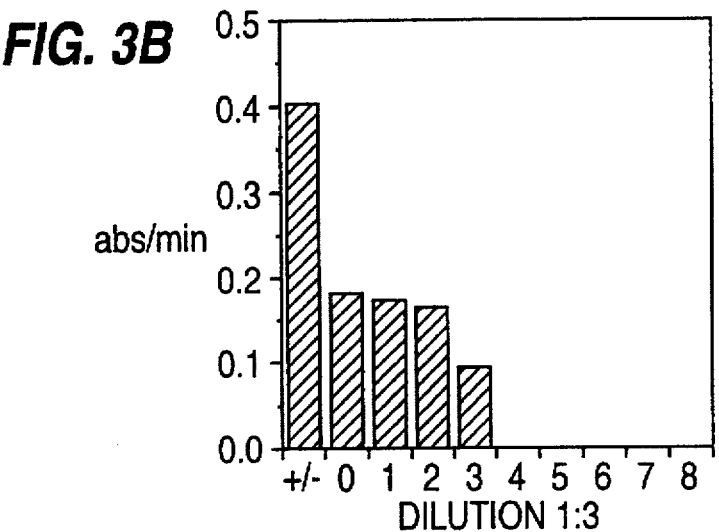
Figure 3C:
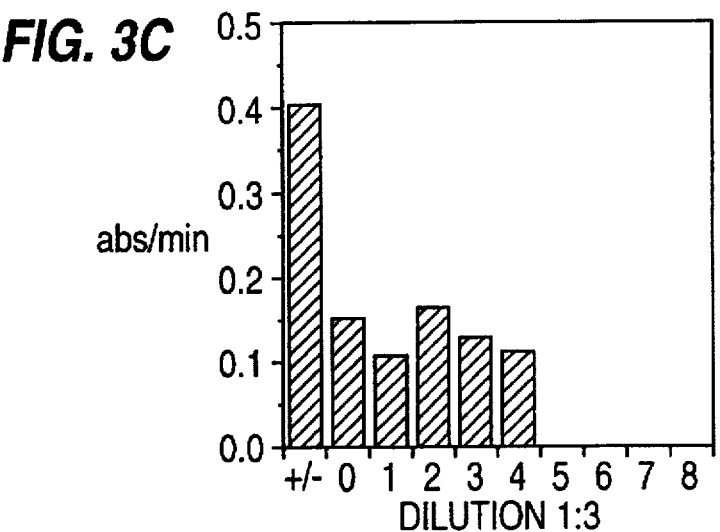
Figure 3D:
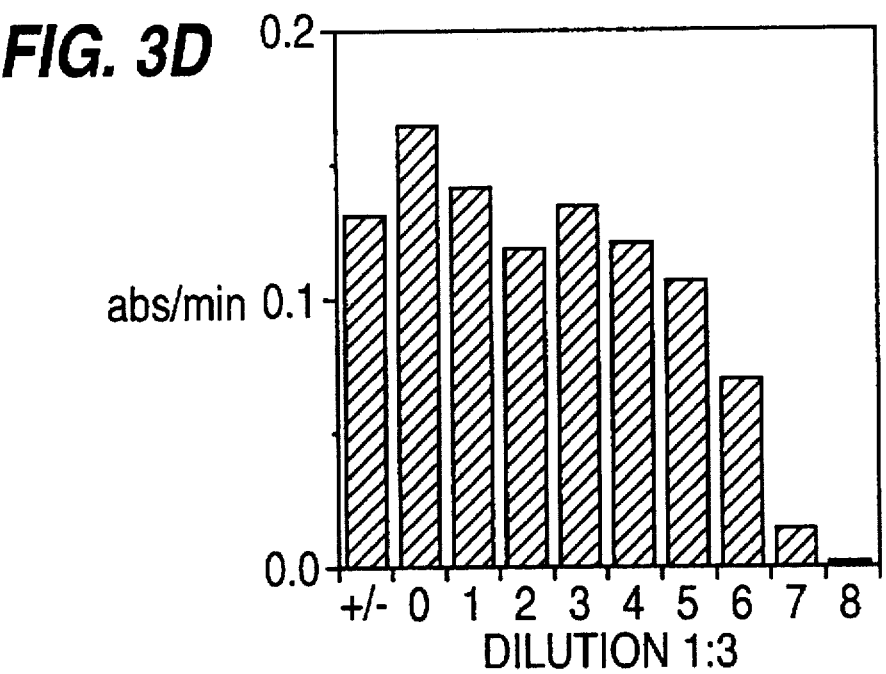
Figure 3E:
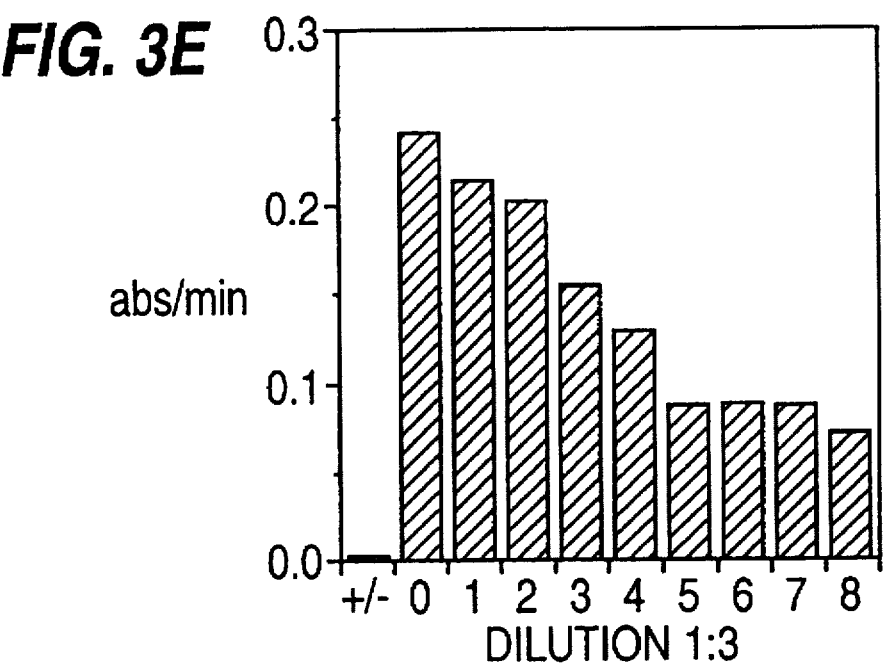

To allow quantification over a relatively broad range (20 to 150000 parasites/sample) without more than nine serial dilutions, the assay was modified by performing 1- to- 3 dilutions. Due to the two-fold lower efficiency for plasmid competitor DNA as compared to genomic DNA (FIG. 3A), 300000 plasmid molecules were added to the sample (dilution 0). Dilutions 1-8 contain approximately 100,000; 33,333; 11,110; 3700; 1240; 410; 140 and 40 competitor molecules, respectively. Several clinical human blood samples from The Gambia (Holmberg supra) were assayed in this manner and independently determined by a microscopical method (Holmberg supra). The results for four independent and representative samples are shown in FIG. 3B,C,D and E. The qualitative DIANA (lane +/−) show that samples B,C and D contain parasites, while sample E is negative. The quantitative DIANA for sample B shows an inflection point between dilutions 3 and 4, which have approximately 11,110 and 3700 competitor molecules, respectively. Because of the two-fold lower amplification efficiency of competitor DNA, this indicates that the sample contains between 5550 and 1850 parasites. This result is in good agreement with the microscopical method which suggested that the sample contained approximately 2600 malaria parasites. Sample C has an inflection point between dilutions 4 and 5 which have approximately 3700 and 1240 competitor molecules, respectively. Because of the two-fold lower amplification efficiency of competitor DNA, this indicates that the sample contains between 1850 and 620 target molecules, respectively, which is in good agreement with the 900 parasites detected with the microscopic method. Sample D, which is known from the microscopic method to contain 40 parasites, has an inflection point between dilutions 7 and 8, containing approximately 140 and 40 competitor molecules respectively. Because of the two-fold lower amplification efficiency of competitor DNA, this indicates that the sample contains between 70 and 20 parasites. This shows that as few as 40 parasites can be detected with the assay. In contrast, all dilutions for sample E show a high colorimetric response, which is expected since this sample did not contain any parasite. It is noted that the absolute values for the individual positive signals vary considerably and this is probably due to variations in efficiencies during the latter part of the PCR procedure. However, this variation does not limit the assay since only the inflexion point must be determined for each sample and thus a high signal to noise ratio is sufficient. In FIG. 3B,C and 3D, the signal in each positive point is indeed high while the background noise is very low. The absolute values between qualitative and quantitative points also differ, probably due to variations of the PCR efficiency with the two different primers (RIT61 and RIT36).

For routine analysis a positive control, e.g. β-globin gene, should be run in parallel to demonstrate that the amplification efficiencies have not been reduced due to presence of inhibitors in the sample.

---

I claim:

1. A method of determining the amount of target DNA in a sample comprising the steps of:
   (a) providing a plurality of aliquots of the sample;
   (b) adding to each aliquot a known amount of competitor DNA, thereby producing aliquots each containing a different ratio of target DNA to competitor DNA, wherein said competitor DNA is the same as the target DNA except that it comprises a recognition site for specific binding by a detector molecule, wherein said detector molecule is not a restriction enzyme and is directly or indirectly linked to a detectable label;
   (c) co-amplifying the target DNA and competitor DNA in each aliquot by the polymerase chain reaction (PCR) using at least one primer which permits immobilization of the co-amplified target and competitor DNA, wherein the amplified competitor DNA contains said recognition site;
   (d) binding said labeled detector molecule to the amplified competitor DNA, thereby producing labeled competitor DNA;
   (e) before or after step (d), immobilizing the co-amplified target and competitor DNA via said PCR primer of step (c); and
   (f) determining the amount of target DNA in the sample by determining the amount of label on the immobilized amplified competitor DNA in each aliquot and generating a titration curve therefrom, determining the inflection point of said titration curve, and using a standard curve to relate the amount of competitor DNA at the inflection point of said titration curve to the amount of target DNA in the sample.

2. The method of claim 1, wherein each aliquot of the sample is at the same dilution, and different amounts of competitor DNA are added to each of said aliquots.

3. The method of claim 2, wherein competitor DNA is added to said aliquots as a series of dilutions.

4. The method of claim 1, further comprising a step wherein qualitative detection of immobilized amplified nucleic acids (DIANA) is performed to determine the presence of target DNA in the sample and/or the total amount of amplified DNA.

5. The method of claim 1, wherein the target DNA is selected from the group consisting of: cDNA produced from RNA, genomic DNA, and mitochondrial DNA.

6. The method of claim 1, wherein said recognition site is introduced by in vitro mutagenesis.

7. The method of claim 1, wherein said detector molecule is a labeled DNA binding protein, wherein said DNA binding protein is not a restriction enzyme.

8. The method of claim 7, wherein said DNA binding protein is lac repressor, and wherein said label is an enzyme.

9. The method of claim 1, wherein said target DNA is of viral, bacterial, protozoal, or fungal origin; and said determining step yields information diagnostic of infection.

10. The method of claim 1, wherein said amplified competitor DNA in step (d) is double-stranded; and wherein said detector molecule binds said double-stranded amplified competitor DNA.

11. The method of claim 1, wherein said competitor DNA comprises a lac operon sequence.

12. A kit for performing the method of claim 1, comprising:
   (a) competitor DNA comprising a recognition site for specific binding by a detector molecule;

(b) a detector molecule that binds to amplified competitor DNA, wherein said detector molecule is not a restriction enzyme and is directly or indirectly linked to a detectable label;

(c) a pair of PCR primers, at least one of which permits immobilization of amplified products;

(d) a polymerase; and (E) buffers for the PCR reaction.

13. The kit of claim 12, wherein said polymerase is a heat stable polymerase.

14. The kit of claim 13, wherein said polymerase is Taq polymerase.

15. The kit of claim 12, further comprising a solid support for immobilizing products of a PCR reaction.

16. The kit of claim 13, further comprising a solid support for immobilizing products of a PCR reaction.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

CGGAATTCCC TCCTCCTGAT ATTGATATTG ATCATAC                          37

( 2 ) INFORMATION FOR SEQ ID NO:2:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

GTTCATGACT GATGTAAATA                                              20

( 2 ) INFORMATION FOR SEQ ID NO:3:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

GGGGATCCTA ATTGTTATCC GCTCACAATT AAAAGAACTT TATCTACAAT AAG         53

( 2 ) INFORMATION FOR SEQ ID NO:4:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

GGGGATCCGG AAGAAGTGGA GGAGACATT                    29

( 2 ) INFORMATION FOR SEQ ID NO:5:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

GTGTCCATTT GCTCTCATAT GC                           22

( 2 ) INFORMATION FOR SEQ ID NO:6:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

AGAAGCTTAA TATTTCTGCC TGTACCAG                     28